United States Patent [19]

Rosenberg

[11] Patent Number: 4,960,419
[45] Date of Patent: Oct. 2, 1990

[54] SURGICAL TISSUE SEPARATION SYSTEM AND SURGICAL KNIFE PARTICULARLY USEFUL THEREIN

[76] Inventor: Lior Rosenberg, 13 Harduf Street, Omer, Beersheba, Israel

[21] Appl. No.: 141,865

[22] Filed: Jan. 11, 1988

[30] Foreign Application Priority Data

Jan. 23, 1987 [IL] Israel ............................. 81376

[51] Int. Cl.$^5$ ................................................ A61B 17/30
[52] U.S. Cl. ...................................... 606/37; 6/167; 30/296.1; 604/22
[58] Field of Search ............... 128/305, 303.14, 303.17; 604/20, 22, 133; 30/296, 330, 331, 337, 340, 342; 606/37, 39, 40, 42, 167

[56] References Cited

U.S. PATENT DOCUMENTS

| | | | |
|---|---|---|---|
| 1,639,996 | 8/1927 | Groff | 128/303.14 |
| 2,215,125 | 10/1940 | Maltz | D24/28 |
| 2,397,257 | 3/1946 | Goland et al. | 604/133 |
| 3,085,332 | 4/1963 | Raybin | 128/305 |
| 3,262,205 | 7/1966 | Arden | 128/305 |
| 3,609,864 | 8/1969 | Bassett | D24/28 |
| 3,906,955 | 9/1975 | Roberts | 128/303.17 |
| 3,974,833 | 8/1976 | Durden, III | 128/303.17 |
| 4,034,761 | 7/1977 | Prater et al. | 128/303.14 |
| 4,562,838 | 1/1986 | Walker | 128/303.17 |
| 4,642,090 | 2/1987 | Utrata | 128/305 |
| 4,719,914 | 1/1988 | Johnson | 128/303.14 |

FOREIGN PATENT DOCUMENTS

1134793 8/1962 Fed. Rep. of Germany .

OTHER PUBLICATIONS

American V. Mueller; Catalog 80; 1980; p. 3.

*Primary Examiner*—C. Fred Rosenbaum
*Assistant Examiner*—William W. Lewis
*Attorney, Agent, or Firm*—Benjamin J. Barish

[57] ABSTRACT

A surgical tissue separation system comprises a handle formed with a bore, a metal blade mounted to one end of the handle and supplied with electricity, and a suction tube connected to the opposite end of the handle by a connector which includes a first section for connection to the suction tube, a second section for connection to a vacuum source for removing smoke and fumes produced by burnt tissue, and a third section for connection to an auxiliary vacuum tip for removing fluids.

14 Claims, 3 Drawing Sheets

SURGICAL TISSUE SEPARATION SYSTEM AND SURGICAL KNIFE PARTICULARLY USEFUL THEREIN

BACKGROUND OF THE INVENTION

The present invention relates to a surgical tissue separation system, and also to surgical knife particularly useful in such a system.

Surgical tissue separation can be achieved according to the following methods: (1) blunt separation or blunt disection (forcing apart); (2) sharp separation (knives); (3) shearing (scissors); (4) thermal separation ("Shaw" scalpel); and (5) electro-thermal separation ("electro-surgery")

The first three methods involve "mechanical" separation of the tissue. When these methods are used, the surgeon aims to separate the tissues in the least traumatic way (the sharp separation or knife being the least traumatic), regardless of the bleeding which may occur from the severed vessels. Part of the bleeding will stop spontaneously (capillary bleeding) while the bleeding from the larger vessels is dealt with by legation or localized cautery.

Methods (4) and (5) above separate the tissues and occluded blood vessels at the same time by cauterization. The thermal knife (e.g., "Shaw" scalpel) is an electrically heated sharp blade having a high electrical resistance, which cauterizes the cut tissues by direct heat transfer from the blade to the tissues. The electro-thermal method ("electrosurgery") transfers the electrical current through the tissues to be removed to produce at the tissue level the high temperature required, the cauterization and tissue separation being effected by the heat generated from the tissue resistance to electrical current.

In the electro-thermal separation method, the electrical current is transferred from the power source to the tissues via metal tips. These tips are shaped in various forms, such as blunt needles, spatulas etc. The surgeon may use these tips to transfer the electrical current to another metallic surgical instrument, usually an artery forceps ("hemostat") or tissue forceps.

In any event, when such tips are used for burning tissues, they produce considerable smoke which obscures the surgeon's view. They also produce fumes which are very unpleasant to the surgeon as well as to everyone else in the operating room.

It is customary today to have on the operating table three separate systems, namely: (1) a mechanical "cutting" device, such as knives, blades, scissors, (2) an electrosurgery system, used for cauterization and cutting, and comprising a metal tip, insulated handle; and connecting insulated conductor; and (3) a suction system, comprising a suction tip, connecting to the vacuum source, and fluid container for removing fluids and the offending smoke and fumes Performing the above functions by means of three separate systems is awkward to the personnel, space-consuming in the operating room, and expensive to produce and maintain.

BRIEF SUMMARY OF THE INVENTION

An object of the present invention is to provide a surgical tissue separation system having advantages in the above respects.

Another object of the invention is to provide a surgical knife having advantages over the surgical knives now in use, and particularly useful in the novel surgical tissue separation system.

According to the present invention, there is provided a surgical tissue separation system comprising: a handle; a metal blade mounted to one end of the handle; means for supplying electricity to the metal blade; the handle being formed with a throughgoing bore from one end to the opposite end; and a suction tube connected to the opposite end of the handle. The suction tube is connected to the handle by a connector which includes a first connector section for connection to the suction tube, a second connector section for connection to a vacuum source for removing smoke and fumes produced by burnt tissue, and a third connector section for connection to an auxiliary vacuum device for removing fluids.

It will thus be seen that when such a surgical system is used as a cutting cautery, the smoke and fumes produced during the cauterization may be continuously removed through the suction tube, thereby permitting the surgeon to have a clearer view of the working area, and also substantially decreasing or eliminating the unpleasant fumes and odors produced during the cauterization of tissue.

The preferred embodiments of the inventions described below include additional features.

According to one feature in the described preferred embodiments, the handle includes an electrical switch for controlling the application of electricity to the metal blade.

According to another feature in the described preferred embodiments, the surgical knife system includes a handle formed with a blade-mounting element at one end, known in the art as a Bard-Parker nose, for mounting a surgical blade, and with a rib spaced axially of the blade-mounting element for abutting engagement with the blade when mounted to the nose, the rib being formed with a V-shaped edge defining two oblique edges facing the nose for mounting a blade having an oblique edge for either a righthand or a lefthand person.

According to a further feature in the described preferred embodiments, the surgical knife includes a metal handle, an outer layer of an elastomeric material over the metal handle and having an outer roughened face of substantially circular cross-section; and a metal blade mounted to one end of the metal handle.

According to a still further feature in the described preferred embodiments, one edge of the blade is formed as a cutting edge as in the usual surgical blades, and the opposite edge of the metal blade is rounded or beveled so as to be used as an electrosurgical tip; in addition, the end of the metal blade is sharpened to produce an auxiliary edge adjacent its juncture with the normal cutting edge, such that both cutting edges may be used both for cutting and for electrosurgery.

According to a still further feature, the connector connected to the end of the handle may be a Y-connector, and may also include a clip for anchoring the connector to a part of the operating table, such as the surgical drapings.

According to a still further feature, the handle includes an ejector element engageable with the end of the blade formed with the oblique edge, and a depressable button carried by the handle which, upon depression, actuates the ejector element to eject the end of the blade out of engagement with the rib.

Further features and advantanges of the invention will be apparent from the description below.

BRIEF DESCRIPTION OF THE DRAWINGS

The invention is herein described, by way of example only, with reference to the accompanying drawings wherein.

DESCRIPTION OF PREFERRED EMBODIMENTS

Figure 1:
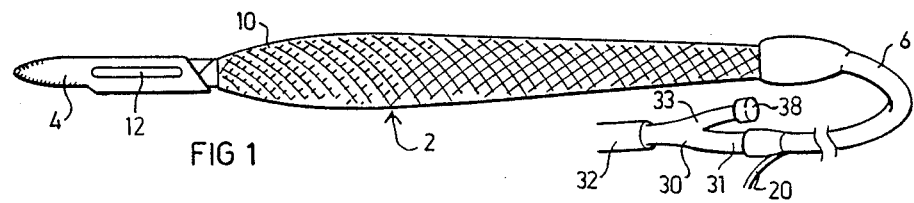
FIG. 1 illustrates one form of surgical knife system having a multi-purpose blade constructed in accordance with the present invention.

The surgical knife system illustrated in FIG. 1 comprises a handle, generally designated 2, having a metal, multi-purpose surgical blade 4 removably attached at one end, as will be described more particularly below The metal blade 4 is also connected to a source of electricity to enable the cutting blade to be used as a cautery for cauterizing blood vessel during cutting. A bore extends through handle 2 from the cutting blade 4 to the opposite end of the handle A suction tube 6 is connected to the opposite end of the handle for removing, via this bore 5, the smoke and fumes produced by the burning of the tissue during the cauterization, in order to maintain a clear vision of the working area to the surgeon, and also to substantially reduce or eliminate the unpleasant fumes and odors produced during the cauterization.

Figure 2:
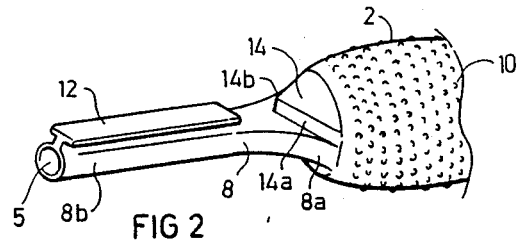
FIG. 2 is an enlarged fragmentary view of the front end of the cutting knife of FIG. 1 but with the surgical multi-purpose blade removed.

As shown more particularly in FIG. 2, handle 2 includes a hollow metal shank 8 of tubular configuration to define bore 5, and an outer layer 10 of an insulating material also of tubular configuration bonded to the inner metal shank 8. The outer insulating layer 10 is made of a soft or hard elastomeric material, such as silcone rubber. Its outer surface is roughened, as by dimpling or knurling, and is of a substantially circular cross-section. Handle 2 is of sufficient length to permit the surgeon to grip the front end of the handle by three fingers, with the rear end of the handle supported between the surgeon's thumb and index finger, in the same manner that a pencil or pen is held. Such a construction permits the surgeon to comfortably grip the handle like a pen or pencil and to conveniently rotate the handle as desired in order to change the orientation of the multi-purpose blade 4 as may be required during the operation.

The construction of the hollow metal shank 8 is more particularly illustrated in FIG. 2. Elastomeric layer 10 is bonded to the main section 8a of the shank. A mounting element 12 is welded to the upper face of the shank nose 8b and extends axially of the shank. This mounting element 12 is adapted to be received within a correspondingly-shaped elongated slot 13 in the multi-purpose blade 4 to firmly secure the cutting blade to the shank, in the same manner as in the Bard-Parker nose.

Shank 8 is further formed with a rib 14 spaced axially of mounting element 12. This rib is adapted to abut the end of the cutting blade 4 when applied to the nose of the shank.

In the conventional cutting knives e.g., as developed by Bard-Parker, a rib corresponding to rib 14 on the handle is formed with a single oblique edge extending for its complete width; this oblique edge abuts the oblique edge 4a of the cutting blade, and permits the cutting blade to be applied only in one orientation with respect to the handle. In the multi-purpose knife illustrated in FIG. 2, however, the front end of rib 14 is formed with a V-shaped surface, to define two oblique edges 14a, 14b, to enable the blade 4 to be applied with its normal cutting edge 4b oriented in one direction with respect to handle 2 (wherein its oblique edge 4a abuts oblique surface 14a of rib 14), or with the normal cutting edge 4b of the blade oriented in the opposite direction (wherein its oblique edge 4a abuts oblique surface 14b of rib 14). Such an arrangement thus permits the blade to be mounted for either righthand surgeons or lefthand surgeons.

The outer insulating layer 10 covers the rear part of rib 14 and is of decreasing thickness to form a smooth juncture with rib 14 and with the remainder of shank 8. Insulating layer 10 is also of decreased thickness at the rear end of the handle also to form a smooth juncture with shank 8. Layer 10 may be provided in different degrees of softness and allows firm gripping by the surgeon.

In the conventional Bard-Parker blade, the back edge 4c of the blade, namely the edge opposite to the usual cutting edge 4b, is flat. However, in the multi-purpose blade 4 illustrated in FIG. 3, this back edge is rounded or bevelled, as shown in FIG. 3b. In addition, the front end of the blade is rounded at this bevelled edge. It is also pointed to serve as an electrosurgical tip, as shown at 4d, and is sharpened for a small length to its outer tip to serve as an auxillary cutting edge, as shown at 4e, to form a two-edged blade at the front end.

The above-described modifications in the construction of blade 4 enable it to be used as a multi-purpose blade, not only for cutting but also for electrical surgery. Thus, the usual cutting edge 4b of the blade may be used for conventional cuts, whereas the sharpened back edge 4e may be used for "back cuts". In addition, the flat side of the blade may be used as a blunt tip for electrosurgery to separate tissue or to cauterize by burning; and the round cross-section of the handle, together with its extended length, enables to be held in the manner of a pen, and thereby facilitates the manipulation of the handle by the surgeon's fingers for all these functions.

In the surgical knife system illustrated in FIGS. 1 and 2, the metal shank 8 serves as the conductor of electricity to the multi-purpose blade 4 when the surgical knife is used as an electrosurgery tip or as a cutting cautery. In addition, the suction tube 6 applied to the rear end of handle 2 serves to conduct electricity to the blade 4 as well as to apply the vacuum through the handle to the working area in order to remove the blood, smoke and fumes produced during the cauterization.

Figure 4:
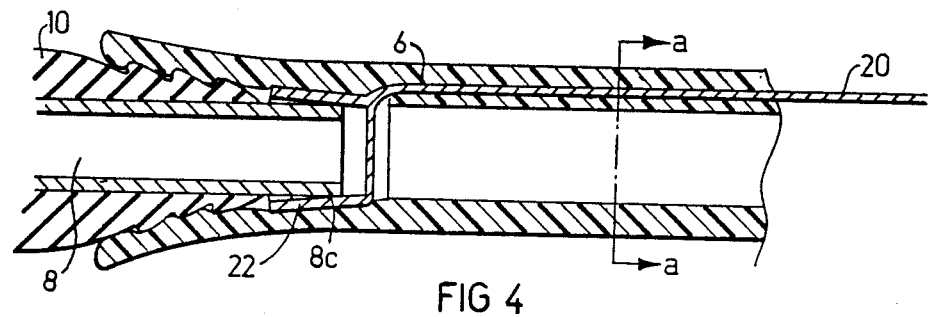
FIG. 4 is an enlarged fragmentary view illustrating the rib end of the cutting knife of FIG. 1, FIG. 4a being a sectional view along lines a—a of FIG. 4.
Figure 4:
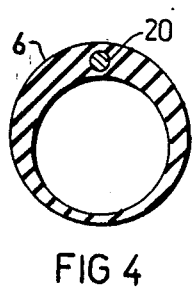

For this purpose, suction tube 6 is of hollow construction, as shown in FIGS. 4 and 4a, and includes an insulated electrical conductor 20 extending through a wall of the tube. One side of electrical conductor 20 is connected to a source of electricity, e.g., via a suitable control switch, which may be provided on the handle 2 or on a foot pedal. The opposite side of the electrical conductor is connected to a metal collar 22 fixed within suction tube 6 at its front end where connected to the rear end of handle 2. The rear end of shank 8 is formed with a metal extension 8c projecting rearwardly through the insulating layer 10 so as to be exposed for contact with collar 22 when suction tube 6 is applied to the rear end of handle 2.

Thus, when suction tube is applied to rear end of handle 2, the suction tube serves to conduct electricity via conductor 20 and shank 8 to the metal blade 4 at the opposite end of the handle, and also applies the suction to the working area of the cutting blade for removing the blood, smoke and fumes produced by the cauterization.

The surgical knife system illustrated in FIG. 1 may also be used for removing blood and other fluids during the surgical operation. For this purpose, there is provided a Y-connector 30 which includes a first connector section 31 for connection to the suction tube 6, a second connector section 32 for connection to a relatively low-powered vacuum source (not shown) for removing the smoke and fumes produced during electosurgery, and a third connector section 33 connectable to an auxiliary suction tip (not shown) for removing blood and other fluids during the surgical operation. Section 32 may be closed by a cap 38 when not in use.

Figure 5:
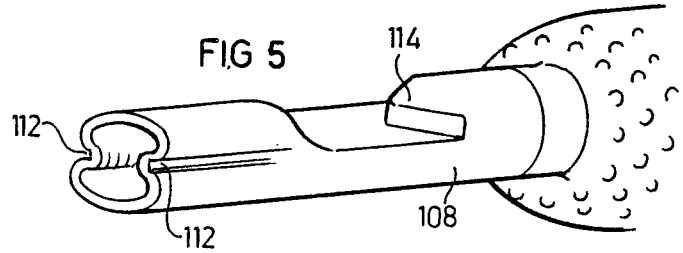
FIG. 5 is a fragmentary view similar to that of FIG. 2 illustrating a modification in the construction of the front end of the surgical knife.

FIG. 5 illustrates a modification in the construction of the front end of the metal shank, therein designated 108. In this modification, the nose end of the shank is formed with, a pair of recesses 112 for receiving the elongated slot 13 of the cutting blade 4 in order to securely fix the blade against rotation. The shank 108 of the handle illustrated in FIG. 5 is also provided with an axially-extending rib 114 having a V-shaped leading edge facing the nose so as to provide the two oblique surfaces (14a, 14b) for mounting the cutting blade for either a righthand surgeon or a lefthand surgeon, in the same manner as described above with respect to FIG. 2.

Figure 6:
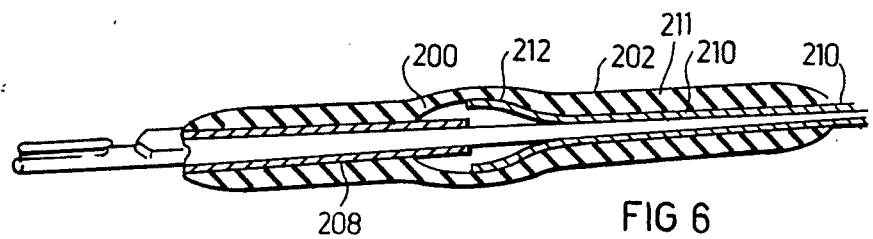
FIG. 6 illustrates a further modification in the construction of the surgical knife for incorporating an electrical switch in the knife handle.

FIG. 6 illustrates further modifications wherein a finger switch, generally designated 200, is provided in the handle 202 to permit the surgeon to conveniently energize or deenergize the cutting blade with electricity. In the arrangement illustrated in FIG. 6, the electricity is supplied to the metal shank 208 via an electrical conductor 210 and an elastic metal spring leaf 212 enclosed by the outer insulating layer 211 of the handle. The outer insulating layer 211 may be of a soft elastromeric material. Elastic spring leaf 212 is normally spaced away from the metal shank 208, but is deflectable by finger pressure into engagement with the metal shank. Electricity may thus be applied via the metal shank to the cutting blade under the convenient finger control of the surgeon.

Figure 7:
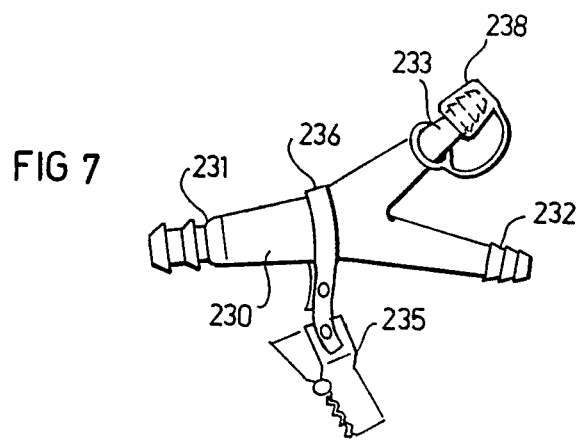
FIG. 7 is a fragmentary view illustrating a variation in the connector device of FIG. 1.

FIG. 7 illustrates a variation wherein the Y-connector, generally designated 230, is provided with a clip 235 attached to the connector by a band 236. Clip 235, such as a conventional alligator clip may be used for anchoring the end of the suction tube (6, FIG. 1) to a convenient point on the operation table, for example to the surgical drapings defining the operating field. Y-connector 230 illustrated in FIG. 7 includes the same three connector sections as described above with respect to FIG. 1, namely connector section 231 for connection to the suction tube (6, FIG. 1), connector 232 for connection to a vacuum source for removing smoke and fumes during an electrosurgical manipulation, and connector section 233 connectable to a vacuum tip for removing blood and other fluids. The latter connector may be closed by a cap 238 when not in use.

Figure 3:
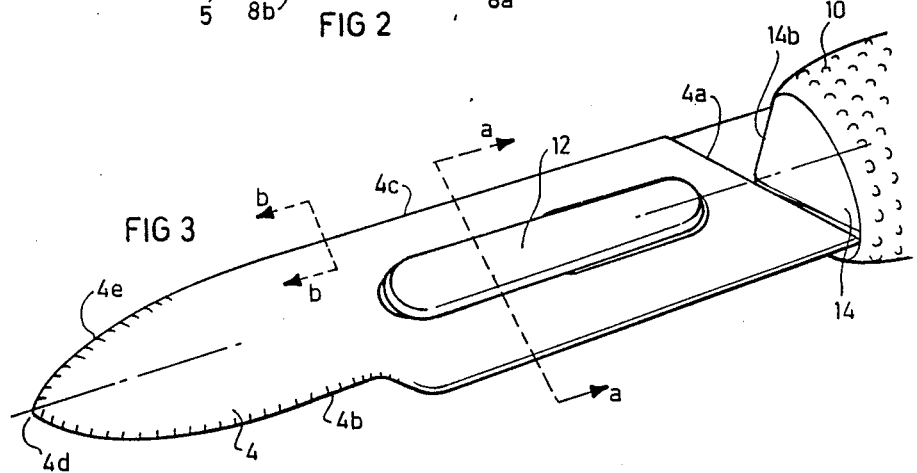
FIG. 3 illustrates the multi-purpose blade used in the knife system of FIG. 1, FIG. 3a being a sectional view along lines a—a, and FIG. 3b being a 3-dimensional view along lines b—b of FIG. 3.
Figures 3A, 3B:
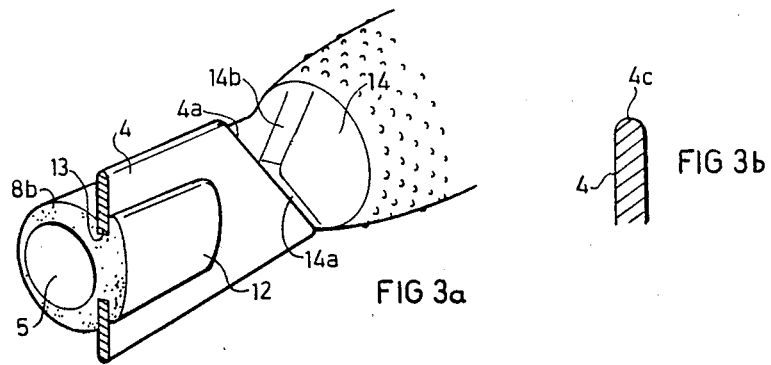
Figure 8:
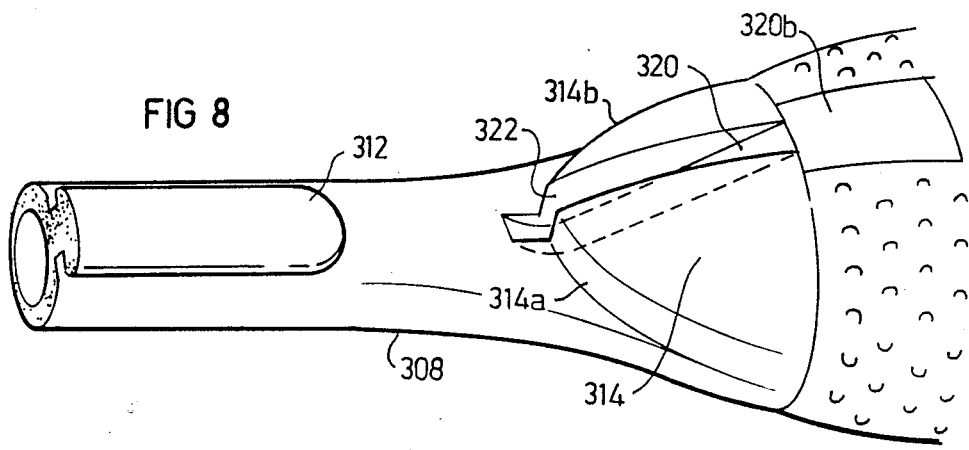
FIG. 8 is an enlarged 3-dimensional fragmentary view illustrating a modification in the construction of the knife handle for accomodating an ejector to facilitate removing the surgical multi-purpose blade.
Figure 9:
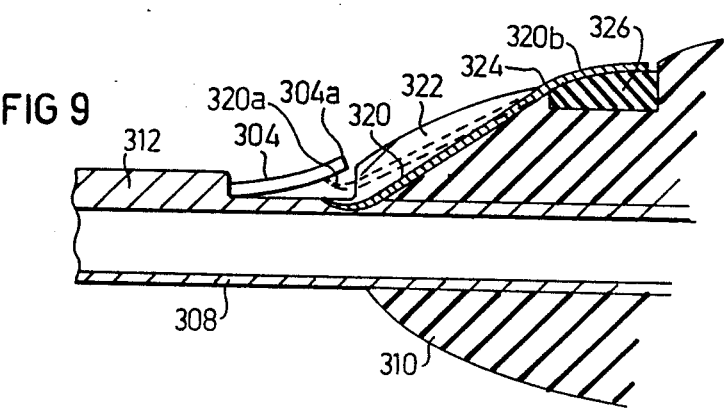
FIG. 9 is a sectional view of the modification of FIG. 8.

FIGS. 8 and 9 illustrate a further feature that may be included in the surgical knife system of the present invention, namely an arrangement to facilitate the removal of the multi-purpose blade (4, FIGS. 1 and 3).

In the arrangement illustrated in FIGS. 8 and 9, the handle shank 308 is formed with a nose 312 for receiving the enlongated slot in the blade (e.g., slot 13 in blade 4, FIG. 3), and also with a V-shaped rib 314 defining the two oblique surfaces 314a and 314b against which the oblique edge (4a FIG. 3) of the blade abuts when mounted to the shank, as described above. In this case, however, a lever 320 is disposed in an inclined groove 322 formed through the apex of rib 314, with the lever being pivotably mounted at the upper end of the groove as shown at 324 in FIG. 9. One end 320a of lever 320 is curved and underlies the end of blade 304 adjacent to its oblique edge 304a, and the opposite end 320b of the lever serves as a finger piece for actuating lever end 320a to eject the respective end of blade 304. Lever 320 is normally urged to the position illustrated in full lines in FIG. 9 by a foam rubber pad 326 or other springy material on the insulating layer 310 over the metal shank 308. The arrangement is such that when finger piece 320b of lever 320 is depressed, the opposite end 320a of the lever moves upwardly to eject the end of blade 304 out of engagement with rib 314. This greatly facilitates the removal of the blade from the handle.

Figure 10:
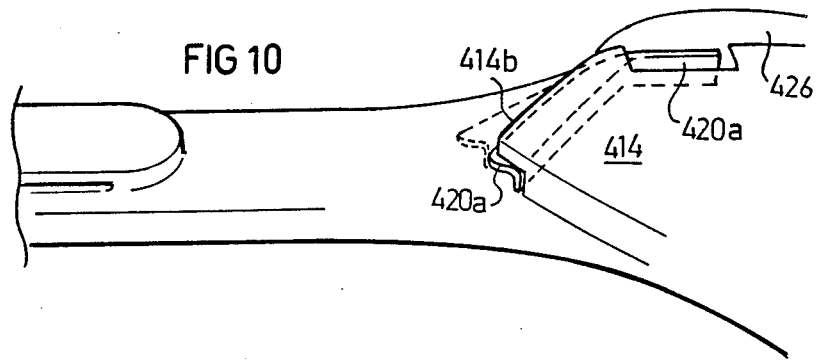
FIG. 10 illustrates another form of blade-ejector arrangement that may be used.
Figure 11:
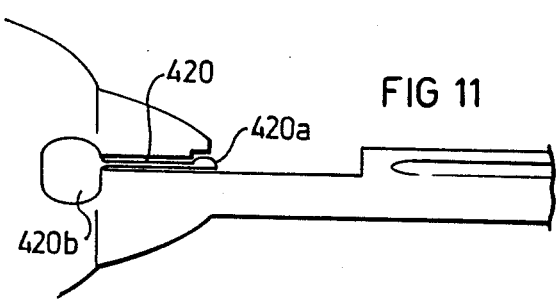
FIG. 11 is a top plan view of the blade-ejector arrangement of FIG. 10.

FIGS. 10 and 12 illustrate a slightly different arrangement for ejecting the end of the blade. In this arrangement, the ejector member, designated 420, includes a wedging element 420a normally received within a recess under oblique edge 414b of the V-shaped rib 414. The ejector member 420 also includes a finger piece 420b which is normally urged to a non-operating position by a foam rubber pad 426 or other spring means. The arrangement illustrated in FIGS. 10 and 11 is such that when the finger piece 420b is depressed, its end 420a moves under the respective end of the blade and wedges it upwardly out of engagement with rib 414, thereby facilitating the manual removal of the blade.

It will thus be seen that in all the above-described embodiments, electricity may be supplied to the multi-purpose blade 4 so as to enable the blade also to be used as an electrosurgical tip or as a cutting cautery. The blood, smoke and fumes produced during the cauterization are evacuated via the suction tube 6, thereby enabling the surgeon to maintain a clear view of the working area, and also substantially decreasing or eliminating the unpleasant odors produced during the cauterization. The construction of handle 2, including the outer, roughened elastomeric layer 10 of circular cross-section, enables the surgeon to conveniently hold the surgical knife in the manner of a pencil with minimal effort, and to conveniently control the orientation and use of the blade to cut, burn or cauterize, as required. The provision of the two oblique surfaces, e.g., 14a, 14b, in the abutting rib 14, enables the cutting blade to be applied for use either by a righthand surgeon or a lefthand surgeon; and the provision of the finger switch 212 (FIG. 6) enables the surgeon to conveniently control the application of electricity to the cutting blade.

In addition, the blade ejector arrangement illustrated in FIGS. 8, 9 and 10 and 11 greatly facilitates the removal of the blade when necessary, by merely depressing the finger piece, which moves the end of the blade out of engagement with the abutting rib.

While the invention has been described with respect to several preferred embodiments, it will be appreciated that many variations, modifications and other applications of the invention may be made. For example, many of the features described herein permitting the blade to be mounted for left or right hand surgeons, and also facilitating the removal of the blade, may also be used in the conventional type surgical knife. Also, the switch in the handle may be a simple micro-switch.

What is claimed is:

1. A surgical tissue separation system comprising: a handle including a hollow metal shank, and a layer of insulating material thereover; a metal blade mounted to one end of the handle; means for supplying electricity to said metal blade; said handle being formed with a throughgoing bore from said one end to the opposite end; and a suction tube connected to the opposite end of the handle by a connector which includes a first connector section for connection to the suction tube, a second connector section for connection to a vacuum source for removing smoke and fumes produced by burnt tissue, and a third connector section for connection to an auxiliary vacuum device for removing fluids.

2. The system according to claim 1, wherein said handle includes an electrically-conductive member extending therethrough from said metal blade to said opposite end for applying electricity to the metal blade.

3. The system according to claim 2, wherein said handle includes an electrical control switch connected to said electrically-conductive member for controlling the application of electricity to said metal blade.

4. The system according to claim 3, wherein said electrical switch includes an elastic metal leaf normally out of engagement with a fixed contact connected to said electrically-conducting member, but deflectable by finger pressure into engagement with said fixed contact for applying electricity to said metal blade.

5. The system according to claim 2, wherein said suction tube includes an electrical conductor extending through a wall thereof, and a metal contact at one end of the tube engageable with the electrically-conductive member extending through the handle for supplying electricity to the metal blade.

6. The system according to claim 1, wherein said insulating material is of an elastomeric material and is formed with a roughened outer surface.

7. The system according to claim 6, wherein the outer face of said elastomeric material is of substantially circular section.

8. The system according to claim 1, wherein said connector further includes a clip for anchoring same to a part of the operating table.

9. The system according to claim 1, wherein said hollow metal shank is formed at said one end of the handle with a blade mounting element extending axially thereof, and a rib spaced axially from said blade mounting element, said rib being formed with a V-shaped end defining two oblique edges facing said blade-mounting element for mounting a blade, having an oblique edge, in either a righthand or a lefthand manner.

10. The system according to claim 9, wherein said blade-mounting element includes a rib integrally formed with said shank and extending axially thereof.

11. The system according to claim 9, wherein said blade-mounting element includes a pair of recesses formed in said shank and extending axially therof.

12. A surgical knife comprising a handle of electrical insulating material; a hollow metal shank extending through the handle from one end to its opposite end; said one end of the shank being formed with a blade-mounting element for mounting a blade; a suction tube of insulating material connected to said opposite end of the handle; and electrical conductor embedded in and extending through a wall of said suction tube; and a metal contact at one end of the tube engageable with said opposite end of the metal shank for supplying electricity to the metal blade when mounted to said blade-mounting element.

13. A surgical knife comprising a handle formed at one end with a blade-mounting element for mounting a blade, and a rib axially of said blade-mounting element for abutting engagement with a blade when mounted thereon, said rib being formed with an oblique edge facing said blade-mounting element engageable with an oblique edge formed in one end of the blade when mounted thereon, an ejector element engageable with the end of the blade formed with said oblique edge, and a depressable button carried by said handle which, upon depression, actuates said ejector element to eject said one end of the blade out of engagement with said rib; said ejector element being a pivotable lever which, upon depression of said button, is pivoted to eject said end of the blade out of engagement with said rib.

14. A surgical knife comprising a handle formed at one end with a blade-mounting element for mounting a blade, and a rib axially of said blade-mounting element for abutting engagement with a blade when mounted thereon, said rib being formed with an oblique edge facing said blade-mounting element engageable with an oblique edge formed in one end of the blade when mounted thereon, an ejector element engageable with the end of the blade formed with said oblique edge, and a depressable button carried by said handle which, upon depression, actuates said ejector element to eject said one end of the blade out of engagement with said rib; said ejector element being a slidable wedge which, upon depression of said button, is slidable laterally of the handle to eject said end of the blade out of engagement with said rib.

* * * * *